US006210695B1

(12) United States Patent
Beerse et al.

(10) Patent No.: US 6,210,695 B1
(45) Date of Patent: *Apr. 3, 2001

(54) LEAVE-ON ANTIMICROBIAL COMPOSITIONS

(75) Inventors: Peter William Beerse, Maineville; Jeffrey Michael Morgan, Springboro; Kathleen Grieshop Baier; Theresa Anne Bakken, both of Cincinnati; Marcus Wayne Evans, Hamilton, all of OH (US)

(73) Assignee: The Procter & Gamble Company, Cincinnati, OH (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/869,129

(22) Filed: Jun. 4, 1997

(51) Int. Cl.⁷ .............................. A01N 25/34; A61K 7/50; A61K 7/40
(52) U.S. Cl. ..................... 424/404; 510/130; 510/131; 510/138
(58) Field of Search .................. 424/404; 510/130, 510/131, 138

(56) References Cited

U.S. PATENT DOCUMENTS

| | | | |
|---|---|---|---|
| 2,999,265 | 9/1961 | Duane et al. | 424/16 |
| 3,057,467 | 10/1962 | Williams | 206/46 |
| 3,141,821 | 7/1964 | Compeau | 167/58 |
| 3,256,200 | 6/1966 | Reller et al. | 252/106 |
| 3,326,808 | 6/1967 | Noseworthy | 252/106 |
| 3,398,826 | 8/1968 | Clancy | 206/46 |
| 3,563,371 | 2/1971 | Heinz | 206/46 |
| 3,650,964 | 3/1972 | Sedliar et al. | 252/106 |
| 3,835,057 | 9/1974 | Cheng et al. | 252/107 |
| 3,867,300 | 2/1975 | Karabinos et al. | 252/106 |
| 3,881,210 | 5/1975 | Drach et al. | 15/104.93 |
| 3,969,258 | 7/1976 | Carandang et al. | 252/106 |
| 4,045,364 | 8/1977 | Richter | 252/106 |
| 4,062,976 | 12/1977 | Michaels | 424/319 |
| 4,067,997 | 1/1978 | Kabara | 424/312 |
| 4,075,350 | 2/1978 | Michaels | 424/316 |
| 4,105,783 | 8/1978 | Yu et al. | 424/283 |
| 4,107,328 | 8/1978 | Michaels | 424/316 |
| 4,118,332 | 10/1978 | Apostolatos et al. | 252/107 |
| 4,183,952 | 1/1980 | Michaels | 424/320 |
| 4,404,040 | 9/1983 | Wang | 134/22.14 |
| 4,406,884 | 9/1983 | Fawzi et al. | 424/81 |
| 4,512,987 | 4/1985 | Schindlery | 514/171 |
| 4,514,385 | 4/1985 | Damani et al. | 424/81 |
| 4,518,593 | 5/1985 | Juvin et al. | 424/195 |
| 4,715,980 | 12/1987 | Lopes et al. | 252/106 |
| 4,732,756 | 3/1988 | Johnson et al. | 428/74 |
| 4,732,797 | 3/1988 | Johnson et al. | 428/74 |
| 4,781,974 | 11/1988 | Bouchette et al. | 428/288 |
| 4,820,698 | 4/1989 | Degenhardt et al. | 514/102 |
| 4,822,604 | 4/1989 | Knoll et al. | 424/70 |
| 4,847,072 | 7/1989 | Bissett et al. | 424/59 |
| 4,891,227 | 1/1990 | Thaman et al. | 424/443 |
| 4,891,228 | 1/1990 | Thaman et al. | 424/443 |
| 4,942,029 | 7/1990 | Scheps | 424/78 |
| 4,971,784 | 11/1990 | Holzel et al. | 424/70 |
| 4,975,217 | 12/1990 | Brown-Skrobot et al. | 252/107 |
| 5,143,720 | 9/1992 | Lopes | 424/55 |
| 5,219,887 | 6/1993 | Andrews et al. | 514/552 |
| 5,234,719 | 8/1993 | Richter et al. | 427/384 |
| 5,280,042 | 1/1994 | Lopes | 514/557 |
| 5,312,559 | * 5/1994 | Kacher et al. | 252/128 |
| 5,378,731 | 1/1995 | Andrews et al. | 514/552 |
| 5,380,756 | 1/1995 | Andrews et al. | 514/552 |
| 5,389,676 | 2/1995 | Michaels | 514/556 |
| 5,441,742 | 8/1995 | Autant et al. | 424/405 |
| 5,480,633 | 1/1996 | Simion et al. | 424/70.1 |
| 5,512,200 | 4/1996 | Garcia | 252/142 |
| 5,547,988 | 8/1996 | Yu et al. | 514/557 |
| 5,595,984 | 1/1997 | Blank | 514/159 |
| 5,607,980 | 3/1997 | McAtee | 514/476 |
| 5,620,694 | 4/1997 | Girardot | 424/402 |
| 5,629,081 | 5/1997 | Richards et al. | 442/96 |

(List continued on next page.)

FOREIGN PATENT DOCUMENTS

| | | | | |
|---|---|---|---|---|
| 0037224 A1 | 10/1981 | (EP) | | C11D/3/48 |
| 0368146 | 5/1990 | (EP) | | C11D/3/50 |
| 0403304 | 12/1990 | (EP) | | A61K/7/06 |

(List continued on next page.)

OTHER PUBLICATIONS

U.S. application No. 08/738,194, Fowler et al., filed Oct. 25, 1996.

U.S. application No. 08/738,669, Fowler et al., filed Oct. 25, 1996.

U.S. application No. 08/738,668, Fowler, filed Oct. 25, 1996.

(List continued on next page.)

Primary Examiner—Raymond Henley, III
Assistant Examiner—Donna Jagoe
(74) Attorney, Agent, or Firm—Stephen T. Murphy; Tara M. Rosnell

(57) ABSTRACT

The present invention relates to a leave-on antimicrobial composition comprising from about 0.001% to about 5.0%, by weight of the leave-on antimicrobial composition, of an antimicrobial active; from about 0.05% to about 10%, by weight of the leave-on antimicrobial composition, of an anionic surfactant; from about 0.1% to about 10%, by weight of the leave-on antimicrobial composition, of a proton donating agent; and from about 0% to about 99.85%, by weight of the leave-on antimicrobial composition, water; wherein the composition is adjusted to a pH of from about 3.0 to about 6.0. The invention also encompasses methods for moisturizing, reducing the number of germs on the skin, and decreasing the spread of transient Gram negative and Gram positive bacteria using the leave-on antimicrobial compositions described herein.

42 Claims, No Drawings

U.S. PATENT DOCUMENTS

| | | | |
|---|---|---|---|
| 5,631,218 | 5/1997 | Allan et al. | 510/423 |
| 5,635,462 | 6/1997 | Fendler et al. | 510/131 |
| 5,681,802 | 10/1997 | Fujiwara et al. | 510/130 |
| 5,700,842 | 12/1997 | Cole | 514/721 |
| 5,744,149 | 4/1998 | Girardot | 424/402 |
| 5,780,020 | 7/1998 | Peterson et al. | 424/65 |
| 5,871,762 * | 2/1999 | Venkitaraman et al. | 424/402 |
| 5,871,763 * | 2/1999 | Luu et al. | 424/402 |
| 5,883,059 * | 3/1999 | Furman et al. | 510/136 |
| 5,972,361 | 10/1999 | Fowler et al. . | |
| 5,980,931 | 11/1999 | Fowler et al. . | |
| 6,063,397 | 5/2000 | Fowler et al. . | |

FOREIGN PATENT DOCUMENTS

| | | | |
|---|---|---|---|
| 0 613 675 | 9/1994 | (EP) | A61K/7/00 |
| 0619074 A1 | 10/1994 | (EP) . | |
| 0670158 A2 | 9/1995 | (EP) | A61K/7/50 |
| 2288811 | 11/1995 | (GB) | C11D/1/831 |
| 2530661 | 6/1996 | (JP) | A61K/7/50 |
| WO 92/18100 | 4/1992 | (WO) | A61K/7/50 |
| WO 93/17558 | 9/1993 | (WO) | A23L/2/38 |
| WO 94/06440 | 9/1993 | (WO) | A61K/31/74 |
| WO 94/18292 | 8/1994 | (WO) | C11D/1/66 |
| WO 95/03028 | 2/1995 | (WO) | A61K/7/00 |
| WO 95/03781 | 2/1995 | (WO) | A61K/7/48 |
| WO 95/32705 | 5/1995 | (WO) | A61K/7/50 |
| WO 95/24179 | 9/1995 | (WO) | A61K/7/00 |
| WO 96/06152 | 2/1996 | (WO) | C11D/3/00 |
| WO 96/06153 | 2/1996 | (WO) | C11D/3/00 |
| WO 96/29049 | 2/1996 | (WO) | A61K/7/48 |
| WO 96/17918 | 6/1996 | (WO) | C11D/1/83 |
| WO 96/29983 | 6/1996 | (WO) | A61K/7/50 |
| WO 96/21426 | 7/1996 | (WO) | A61K/7/50 |
| WO 96/25913 | 8/1996 | (WO) | A61K/7/16 |
| WO 97/00676 | 1/1997 | (WO) | A61K/31/19 |
| WO 97/03647 | 2/1997 | (WO) | A61K/7/50 |
| WO 97/07781 | 3/1997 | (WO) | A61K/7/50 |
| WO 97/09957 | 3/1997 | (WO) | A61K/7/00 |
| WO 97/14406 | 4/1997 | (WO) | A61K/7/50 |
| WO 97/16066 | 5/1997 | (WO) . | |
| WO 97/16168 | 5/1997 | (WO) | A61K/7/50 |
| WO 98/18445 | 5/1998 | (WO) | A61K/7/50 |

OTHER PUBLICATIONS

U.S. application No. 08/738,145, Fowler, filed Oct. 25, 1996.

U.S. application No. 08/740,280, Fowler et al., filed Oct. 25, 1996.

U.S. application No. 08/738,131, Fowler, et al.

Ananthapadmanabhan, K.P., Yu, K.K, Meyers, C.L. and Aronson, M.P., Binding of Surfactants to Stratum Corneum, (1996), *J. Soc. Cosmet. Chem.*, vol. 47, pp. 185–200.

Antoine, J.L., Contreras, J.L. and Van Neste, D.J., pH Influence of Surfactant–induced Skin Irritation, (1989), *Dermatosen 37*, pp. 96–100.

Axe, Douglas D. and Bailey, James E., Transport of Lactate and Acetate Through the Energized Cytoplasmic Membrane of *Escherichia coli*, (1995), *Biotechnology and Bioengineering*, vol. 47, pp. 8–19.

Baker, Zelma, Ph.D., Harrison, R.W., Ph.D., and Miller, Benjamin F., M.D., Action of Synthetic Detergents on the Metabolism of Bacteria, (1940), *The Journal of Exp. Med.*, 73, pp. 249–271.

Bandelin, Fred J., The Effect of pH on the Efficiency of Various Mold Inhibiting Compounds, (1958), *The Journal of the American Pharmaceutical Association*, vol. XLVII, No. 10, pp. 96–98.

Bender, Max, Interfacial Phenomenia in Biological Systems, (1991), pp. 1–49.

Blank, Irvin H., PhD, Measurement of pH of the Skin Surface, (1939), *The Journal of Investigatvie Dermatology*, vol. 2, pp. 75–79.

Brown, M.R.W., The Role of the Cell Envelope in Resistance, *Resistance of Pseudomonas Aeruginosa*, pp. 70–107.

Buckley, D. and Thomas, J., Antimicrobial Activity of Sodium n–Alkylsalicylates, (1971), *Applied Microbiology*, vol. 21, No. 4, pp. 565–568.

Dychdala, G.R. and Lopes, John A., Surface–Active Agents: Acid–Anionic Compounds, *Disinfectants and Antiseptics: A. By Chemical Type*, pp. 256–262.

Flexner, Simon, M.D., Rous, Peyton, M.D., Gasser, Herbert, M.D., The Journal of Experimental Medicine, (1941), V74, pp. 611–620.

Fukahori M., Akatsu S., Sato H., and Yotsuyanagi T., Relationship Between Uptake of p–hydroxybenzoic acid esters by *Escherichia coli* and Antibacterial Activity, (1996), Chem. Pharm. Bull., vol 44(8), pp. 1567–1570.

Gershenfeld, Louis and Milanick, Vera Elaine, Bactericidal and Bacteriostatic Properties of Surface Tension Depressants, (1941), *American Journal of Pharmaceuticals*, 113, pp. 306–326.

Gershenfeld, Louis, D. Sc. and Perlstein, David, M. Sc., Significance of Hydrogen–ion Concentration in the Evaluation of the Bactericidal Efficiency of Surface Tension Depressants, (1941), *American Journal of Pharmaceuticals*, 113, pp. 89–92.

Gershenfeld, Louis and Witlin, Bernard, Surface Tension Reducents by Bactericidal Solutions: Their In Vitro and In Vivo Efficiencies, (1941), *American Journal of Pharmaceuticals*, 113, pp. 215–236.

Glassman, Harold N., Surface Active Agents and Their Application in Bacteriology, (1948), *Bacteriological Review*, V. 13, pp. 105–148.

Haque H. and A. D. Russell, Cell Envelopes of Gram Negative Bacteria: Compositions, Response to Chelating Agents and Suscpetibility of Whole Cells to Antibacterial Agents, J. Appl. Bact., (1976), vol 40, pp. 89–99.

Hotchkiss, Rollin D., The Nature of the Bactericidal Actin of Surface Active Agents, *Annals New York Academy of Sciences*, pp. 479–498.

Hubbard, A.W., Moore, L.J., Clothier, R.H., Sulley, J. and Rollin, K.A., Use of In Vitro Methodology to Predict the Irritancy Potential of Surfactants, (1994), *Toxic. in Vitro*, vol. 8, No. 4, pp. 689–691.

Kabara, Jon J., Structure–function relationships of surfactants as antimicrobial agents, (1978), *Journal of the Society of Cosmetic Chemists*, 29, pp. 733–741.

Kostenbauder, Harry B., Physical Factors Influencing the Activity of Antimicrobial Agents, pp. 59–71.

McDade, Joseph J. and Hall, Lawrence B., Survival of Gram–Negative Bacterial in the Environment, (1964), *Am. J. Hyg*, vol. 80, pp. 192–204.

Meincke, B.E., Kranz, R.G., Lynch, D.L., Effect of Irgasan on Bacterial Growth and Its Absorption Into the Cell Wall, (1980), *Microbios*, 28, pp. 133–147.

Ordal, E.J. and Deromedi, F., Studies on the Action of Wetting Agents on Microorganisms, (1943), *Journal of Applied Bacteriology 45*, pp. 293–299.

Rahn, Otto and Conn, Jean E., Effect of Increase in Acidity on Antiseptic Efficiency, (1944), *Industrial Engineering/Chemistry*, Soc. 36 (2) pp. 185–187.

Regos, J., Zak, O., Solf, R., Vischer, W.A. and Weirich, E.G., Antimicrobial Spectrum of Triclosan, a Broad–Spectrum Antimicrobial Agent for Topical Application, (1979), *Dermatologica 158*, pp. 72–29.

Russell, James B., Resistance of *Streptococcus bovis* to Acetic Acid at Low pH: Relationship between Intracellular pH and Anion Accumulation, (1991), *Applied and Environmental Microbiology*, vol. 57. No. 1, pp. 255–259.

Russell, J.B., Another explanation for the toxicity of fermentation acids at low pH: anion accumulation versus uncoupling, (1992), *Journal of Applied Bacteriology*, 73, pp. 363–370.

Scalzo, Marcello, Orlandi, Clelia, Simonetti, Nicola and Cerreto, Felice, Study of Interaction Effects of Polyacrylic Acid Polymers (Carbolpol 940) on Antimicrobial Activity of Methyl Parahyroxybenzoate Against Some Gram–negative, Gram–positive Bacteria and Yeast, (1996), *J. Pharm. Pharmacol*, pp. 1201–1205.

Schoenberg, Tom, Formulating Mild Body Washes, (1996), *happi*, pp. 53–56.

Shenna, A.Z. and Stiles, M.E., Immediate and Residual (Substantive) Efficacy of Germicidal Hand Wash Agents, (1983), *Journal of Food Protection*, vol. 46, No. 7, pp. 629–636.

Stotts, Jane, M.S. and Kooistra, John A., PhD., Micrococcaceae of Normal Human Skin Before and After Use of an Antibacterial Soap, (1970).

Wortzman, Mitchell S., PhD, Evaluation of Mild Skin Cleansers, (1991), *Dermatologic Clinics*, vol. 9, No. 1, pp. 35–44.

Young, K.M. and Foegeding, Peggy M., Acetic, latic and citric acids and pH inhibition of *Listeria monocytogenes* Scott A and the Effect on Intracellular pH, (1993), *Journal of Applied Bacteriology*, 74, pp. 515–520.

Ciba Giegy Trade Literature: Basic Formulation for Hand Disinfection 89/42/01, 89/42/05, & 91/01/49.

Head & Shoulders D Product: Finished Product Standard No. 8427 & 8428 dated Dec. 20, 1991.

Oil of Olay Age defying Series Daily Renewal Cleanser with Gentle Microbeads (Copy of Product).

U.S. application No. 08/529,258, Glenn et al, filed Sep. 15, 1995.

U.S. application No. 08/959,969, Glenn et al, filed Oct. 24, 1997.

U.S. application No. 08/868,783, Beerse et al, filed Jun. 4, 1997.

U.S. application No. 08/868,695, Beerse et al, filed Jun. 4, 1997.

U.S. application No. 08/969,049, Beerse et al, filed Nov. 12, 1997.

U.S. application No. 08/868,982, Beerse et al, filed Jun. 4, 1997.

U.S. application No. 08/869,302, Beerse et al, filed Jun. 4, 1997.

U.S. application No. 08/869,300, Beerse et al, filed Jun. 4, 1997.

U.S. application No. 08/869,071, Beerse et al, filed Jun. 4, 1997.

U.S. application No. 08/869,116, Beerse et al, filed Jun. 4, 1997.

U.S. application No. 08/869,688, Beerse et al, filed Jun. 4, 1997.

U.S. application No. 08/969,057, Beerse et al, filed Nov. 12, 1997.

U.S. application No. 08/868,687, Beerse et al, filed Jun. 4, 1997.

U.S. application No. 08/868,717, Beerse et al, filed Jun. 4, 1997.

U.S. application No. 08/869,301, Beerse et al, filed Jun. 4, 1997.

U.S. application No. 08/868,718, Beerse et al, filed Jun. 4, 1997.

U.S. application No. 08/967,972, Beerse et al, filed Nov. 12, 1997.

U.S. application No. 08/869,303, Beerse et al, filed Jun. 4, 1997.

U.S. application No. 08/869,304, Beerse et al, filed Jun. 4, 1997.

U.S. application No. 08/969,007, Beerse et al, filed Nov. 12, 1997.

U.S. application No. 08/869,117, Beerse et al, filed Jun. 4, 1997.

* cited by examiner

LEAVE-ON ANTIMICROBIAL COMPOSITIONS

TECHNICAL FIELD

The present invention relates to leave-on antimicrobial compositions which provide enhanced antimicrobial effectiveness compared to prior art compositions. Specifically, the leave-on compositions of the invention provide previously unseen residual effectiveness against transient Gram negative bacteria, improved residual effectiveness against Gram positive bacteria and improved immediate germ removal upon use.

BACKGROUND OF THE INVENTION

Human health is impacted by many microbial entities. Inoculation by viruses and bacteria cause a wide variety of sicknesses and ailments. Media attention to cases of food poisoning, strep infections, and the like is increasing public awareness of microbial issues.

It is well known that the washing of hard surfaces, food (e.g. fruit or vegetables) and skin, especially the hands, with antimicrobial or non-medicated soap, can remove many viruses and bacteria from the washed surfaces. Removal of the viruses and bacteria is due to the surfactancy of the soap and the mechanical action of the wash procedure. Therefore, it is known and recommended that the people wash frequently to reduce the spread of viruses and bacteria.

Bacteria found on the skin can be divided into two groups: resident and transient bacteria. Resident bacteria are Gram positive bacteria which are established as permanent microcolonies on the surface and outermost layers of the skin and play an important, helpful role in preventing the colonization of other, more harmful bacteria and fungi.

Transient bacteria are bacteria which are not part of the normal resident flora of the skin, but can be deposited when airborne contaminated material lands on the skin or when contaminated material is brought into physical contact with it. Transient bacteria are typically divided into two subclasses: Gram positive and Gram negative. Gram positive bacteria include pathogens such as *Staphylococcus aureus, Streptococcus pyogenes* and *Clostridium botulinum.* Gram negative bacteria include pathogens such as Salmonella, *Escherichia coli,* Klebsiella, Haemophilus, *Pseudomonas aeruginosa, Proteus* and *Shigella dysenteriae.* Gram negative bacteria are generally distinguished from Gram positive by an additional protective cell membrane which generally results in the Gram negative bacteria being less susceptible to topical antibacterial actives.

Antimicrobial cleansing products have been marketed in a variety of forms for some time. Forms include deodorant soaps, hard surface cleaners, and surgical disinfectants. These traditional rinse-off antimicrobial products have been formulated to provide bacteria removal during washing. The antimicrobial soaps have also been shown to provide a residual effectiveness against Gram positive bacteria, but limited residual effectiveness versus Gram negative bacteria. By residual effectiveness it is meant that bacteria growth on a surface is controlled for some period of time following the washing/rinsing process. Antimicrobial liquid cleansers are disclosed in U.S. Pat. Nos. 4,847,072, Bissett et al., issued Jul. 11, 1989, 4,939,284, Degenhardt, issued Jul. 3, 1990 and 4,820,698, Degenhardt, issued Apr. 11, 1989, all patents being incorporate herein by reference.

Some of these traditional products, especially the hard surface cleaners and surgical disinfectants, utilize high levels of alcohol and/or harsh surfactants which have been shown to dry out and irritate skin tissues. Ideal personal cleansers should gently cleanse the skin, cause little or no irritation, and not leave the skin overly dry after frequent use and preferably should provide a moisturizing benefit to the skin.

Finally, these traditional antimicrobial compositions have been developed for use in a washing process with water. This limits their use to locations with available water.

Leave-on, topical lotions have been used in the past to moisturize skin. However, these leave-on compositions have not provided antimicrobial protection against transient Gram positive or Gram negative organisms.

PCT application WO 92/18100, Keegan et al., published Oct. 29, 1992 and PCT application WO 95/32705, Fujiwara et al., published Dec. 7, 1995 teach non-wipe liquid skin cleansers comprising mild surfactants, antibacterial agents and acidic compounds to buffer the pH, which provide improved germ hostility. However, the use of the acid compounds for only pH adjustment therein, results in compositions which do not deliver the undissociated acid required to provide improved antimicrobial benefits. This situation is compounded in Keegan and Fujiwara by the preference of mild surfactants, including nonionic surfactants. Neither Keegan nor Fujiwara teach the use of their compositions in a form which can be used without available water, e.g. a leave-on composition. U.S. Pat. No. 3,141,821, issued to Compeau, Jul. 21, 1964 and Irgasan DP 300 (Triclosan®) technical literature from Ciba-Giegy, Inc., "Basic Formulation for Hand Disinfection 89/42/01" set forth antibacterial skin cleanser compositions which could provide improved antibacterial effectiveness using certain anionic surfactants, antimicrobial actives and acids. However, the selection of highly active surfactants results in personal cleansing compositions which are drying and harsh to the skin. Again, neither reference teaches the use of antimicrobial compositions in a form which can be used without available water, e.g. a leave-on.

Given the severe health impacts of bacteria like Salmonella, *Escherichia coli* and Shigella, it would be highly desirable to formulate antimicrobial cleansing products which provides improved reduction of these germs on the skin and improved residual effectiveness versus these transient bacteria, which are mild to the skin and which can be used without water. Existing products have been unable to deliver all of these benefits.

Applicants have found that leave-on antimicrobial compositions which provide such mildness and antimicrobial benefits can be formulated by using known antibacterial actives in combination with specific organic and/or inorganic acids as proton donating agents, and specific anionic surfactants, all of which are deposited on the skin. The deposited proton donating agent and anionic surfactant enhance the selected active, to provide a new level of hostility to bacteria contacting the skin.

SUMMARY OF THE INVENTION

The present invention relates to a leave-on antimicrobial composition comprising from about 0.001% to about 5.0%, by weight of the leave-on antimicrobial composition, of an antimicrobial active; from about 0.05% to about 10%, by weight of the leave-on antimicrobial composition, of an anionic surfactant; from about 0.1% to about 10%, by weight of the leave-on antimicrobial composition, of a proton donating agent; and from about 0% to about 99.85%, by weight of the leave-on antimicrobial composition, water;

wherein the composition is adjusted to a pH of from about 3.0 to about 6.0. The invention also encompasses methods for cleansing, reducing the number of germs on the skin and decreasing the spread of transient Gram negative and Gram positive bacteria using the leave-on antimicrobial compositions described herein.

DETAILED DESCRIPTION OF THE INVENTION

The leave-on antimicrobial compositions of the present invention are highly efficacious for providing improved germ reduction, and residual antimicrobial effectiveness versus transient bacteria, are mild to the skin and can be used without additional available water. The term "leave-on antimicrobial composition" is used herein to mean products suitable for application to the human skin for the purpose controlling the growth and viability of transient bacteria on the skin.

The compositions of the present invention can also be useful for treatment of acne. As used herein "treating acne" means preventing, retarding and/or arresting the process of acne formation in mammalian skin.

The compositions of the invention can also potentially be useful for providing an essentially immediate (i.e., acute) visual improvement in skin appearance following application of the composition to the skin. More particularly, the compositions of the present invention are useful for regulating skin condition, including regulating visible and/or tactile discontinuities in skin, including but not limited to visible and/or tactile discontinuities in skin texture and/or color, more especially discontinuities associated with skin aging. Such discontinuities may be induced or caused by internal and/or external factors. Extrinsic factors include ultraviolet radiation (e.g., from sun exposure), environmental pollution, wind, heat, low humidity, harsh surfactants, abrasives, and the like. Intrinsic factors include chronological aging and other biochemical changes from within the skin. Regulating skin condition includes prophylactically and/or therapeutically regulating skin condition. As used herein, prophylactically regulating skin condition includes delaying, minimizing and/or preventing visible and/or tactile discontinuities in skin. As used herein, therapeutically regulating skin condition includes ameliorating, e.g., diminishing, minimizing and/or effacing, such discontinuities. Regulating skin condition involves improving skin appearance and/or feel, e.g., providing a smoother, more even appearance and/or feel. As used herein, regulating skin condition includes regulating signs of aging. "Regulating signs of skin aging" includes prophylactically regulating and/or therapeutically regulating one or more of such signs (similarly, regulating a given sign of skin aging, e.g., lines, wrinkles or pores, includes prophylactically regulating and/or therapeutically regulating that sign). "Signs of skin aging" include, but are not limited to, all outward visibly and tactilely perceptible manifestations as well as any other macro or micro effects due to skin aging. Such signs may be induced or caused by intrinsic factors or extrinsic factors, e.g., chronological aging and/or environmental damage. These signs may result from processes which include, but are not limited to, the development of textural discontinuities such as wrinkles, including both fine superficial wrinkles and coarse deep wrinkles, skin lines, crevices, bumps, large pores (e.g., associated with adnexal structures such as sweat gland ducts, sebaceous glands, or hair follicles), scaliness, flakiness and/or other forms of skin unevenness or roughness, loss of skin elasticity (loss and/or inactivation of functional skin elastin), sagging (including puffiness in the eye area and jowls), loss of skin firmness, loss of skin tightness, loss of skin recoil from deformation, discoloration (including undereye circles), blotching, sallowness, hyperpigmented skin regions such as age spots and freckles, keratoses, abnormal differentiation, hyperkeratinization, elastosis, collagen breakdown, and other histological changes in the stratum corneum, dermis, epidermis, the skin vascular system (e.g., telangiectasia or spider vessels), and underlying tissues, especially those proximate to the skin.

All percentages and ratios used herein, unless otherwise indicated, are by weight and all measurements made are at 25° C., unless otherwise designated. The invention hereof can comprise, consist of, or consist essentially of, the essential as well as optional ingredients and components described therein.

I. Ingredients

The leave-on antimicrobial compositions of the present invention comprise an antimicrobial active, an anionic surfactant, and a proton donating agent. Each of these ingredients is described in detail as follows.

A. Antimicrobial Active

The leave-on antimicrobial composition of the present invention comprises from about 0.001% to about 5%, preferably from about 0.05% to about 2%, and more preferably from about 0.1% to about 1%, by weight of the leave-on antimicrobial composition, of an antimicrobial active. The exact amount of antibacterial active to be used in the compositions will depend on the particular active utilized since actives vary in potency. Non-cationic actives are required in order to avoid interaction with the anionic surfactants of the invention. Given below are examples of non-cationic antimicrobial agent which are useful in the present invention.

Pyrithiones, especially the zinc complex (ZPT)
Octopirox®
Dimethyldimethylol Hydantoin (Glydant®)
Methylchloroisothiazolinone/methylisothiazolinone (Kathon CG®)
Sodium Sulfite
Sodium Bisulfite
Imidazolidinyl Urea (Germall 115®)
Diazolidinyl Urea (Germall II®)
Benzyl Alcohol
2-Bromo-2-nitropropane-1,3-diol (Bronopol®)
Formalin (formaldehyde)
Iodopropenyl Butylcarbamate (Polyphase P100®)
Chloroacetamide
Methanamine
Methyldibromonitrile Glutaronitrile (1,2-Dibromo-2,4-dicyanobutane or Tektamer®)
Glutaraldehyde
5-bromo-5-nitro-1,3-dioxane (Bronidox®)
Phenethyl Alcohol
o-Phenylphenol/sodium o-phenylphenol
Sodium Hydroxymethylglycinate (Suttocide A®)
Polymethoxy Bicyclic Oxazolidine (Nuosept C®)
Dimethoxane
Thimersal
Dichlorobenzyl Alcohol
Captan
Chlorphenenesin Dichlorophene
Chlorbutanol
Glyceryl Laurate
Halogenated Diphenyl Ethers
   2,4,4'-trichloro-2'-hydroxy-diphenyl ether (Triclosan® or TCS)
   2,2'-dihydroxy-5,5'-dibromo-diphenyl ether
Phenolic Compounds
   Phenol
   2-Methyl Phenol
   3-Methyl Phenol
   4-Methyl Phenol
   4-Ethyl Phenol
   2,4-Dimethyl Phenol
   2,5-Dimethyl Phenol
   3,4-Dimethyl Phenol
   2,6-Dimethyl Phenol
   4-n-Propyl Phenol
   4-n-Butyl Phenol
   4-n-Amyl Phenol
   4-tert-Amyl Phenol
   4-n-Hexyl Phenol
   4-n-Heptyl Phenol
Mono- and Poly-Alkyl and Aromatic Halophenols
   p-Chlorophenol
   Methyl p-Chlorophenol
   Ethyl p-Chlorophenol
   n-Propyl p-Chlorophenol
   n-Butyl p-Chlorophenol
   n-Amyl p-Chlorophenol
   sec-Amyl p-Chlorophenol
   n-Hexyl p-Chlorophenol
   Cyclohexyl p-Chlorophenol
   n-Heptyl p-Chlorophenol
   n-Octyl p-Chlorophenol
   o-Chlorophenol
   Methyl o-Chlorophenol
   Ethyl o-Chlorophenol
   n-Propyl o-Chlorophenol
   n-Butyl o-Chlorophenol
   n-Amyl o-Chlorophenol
   tert-Amyl o-Chlorophenol
   n-Hexyl o-Chlorophenol
   n-Heptyl o-Chlorophenol
   o-Benzyl p-Chlorophenol
   o-Benxyl-m-methyl p-Chlorophenol
   o-Benzyl-m, m-dimethyl p-Chlorophenol
   o-Phenylethyl p-Chlorophenol
   o-Phenylethyl-m-methyl p-Chlorophenol
   3-Methyl p-Chlorophenol
   3,5-Dimethyl p-Chlorophenol
   6-Ethyl-3-methyl p-Chlorophenol
   6-n-Propyl-3-methyl p-Chlorophenol
   6-iso-Propyl-3-methyl p-Chlorophenol
   2-Ethyl-3,5-dimethyl p-Chlorophenol
   6-sec-Butyl-3-methyl p-Chlorophenol
   2-iso-Propyl-3,5-dimethyl p-Chlorophenol
   6-Diethylmethyl-3-methyl p-Chlorophenol
   6-iso-Propyl-2-ethyl-3-methyl p-Chlorophenol
   2-sec-Amyl-3,5-dimethyl p-Chlorophenol
   2-Diethylmethyl-3,5-dimethyl p-Chlorophenol
   6-sec-Octyl-3-methyl p-Chlorophenol
   p-Chloro-m-cresol
   p-Bromophenol
   Methyl p-Bromophenol
   Ethyl p-Bromophenol
   n-Propyl p-Bromophenol
   n-Butyl p-Bromophenol
   n-Amyl p-Bromophenol
   sec-Amyl p-Bromophenol
   n-Hexyl p-Bromophenol
   Cyclohexyl p-Bromophenol
   o-Bromophenol
   tert-Amyl o-Bromophenol
   n-Hexyl o-Bromophenol
   n-Propyl-m,m-Dimethyl o-Bromophenol
   2-Phenyl Phenol
   4-Chloro-2-methyl phenol
   4-Chloro-3-methyl phenol
   4-Chloro-3,5-dimethyl phenol
   2,4-Dichloro-3,5-dimethylphenol
   3,4,5,6-Terabromo-2-methylphenol
   5-Methyl-2-pentylphenol
   4-Isopropyl-3-methylphenol
   Para-chloro-meta-xylenol (PCMX)
   Chlorothymol
   Phenoxyethanol
   Phenoxyisopropanol
   5-Chloro-2-hydroxydiphenylmethane
Resorcinol and its Derivatives
   Resorcinol
   Methyl Resorcinol
   Ethyl Resorcinol
   n-Propyl Resorcinol
   n-Butyl Resorcinol
   n-Amyl Resorcinol
   n-Hexyl Resorcinol
   n-Heptyl Resorcinol
   n-Octyl Resorcinol
   n-Nonyl Resorcinol
   Phenyl Resorcinol
   Benzyl Resorcinol
   Phenylethyl Resorcinol
   Phenylpropyl Resorcinol
   p-Chlorobenzyl Resorcinol
   5-Chloro 2,4-Dihydroxydiphenyl Methane
   4'-Chloro 2,4-Dihydroxydiphenyl Methane
   5-Bromo 2,4-Dihydroxydiphenyl Methane
   4'-Bromo 2,4-Dihydroxydiphenyl Methane
Bisphenolic Compounds
   2,2'-Methylene bis (4-chlorophenol)
   2,2'-Methylene bis (3,4,6-trichlorophenol)
   2,2'-Methylene bis (4-chloro-6-bromophenol)
   bis (2-hydroxy-3,5-dichlorophenyl) sulphide
   bis (2-hydroxy-5-chlorobenzyl)sulphide
Benzoic Esters (Parabens)
   Methylparaben
   Propylparaben
   Butylparaben
   Ethylparaben
   Isopropylparaben
   Isobutylparaben
   Benzylparaben
   Sodium Methylparaben
   Sodium Propylparaben
Halogenated Carbanilides
   3,4,4'-Trichlorocarbanilides (Triclocarban® or TCC)
   3-Trifluoromethyl-4,4'-dichlorocarbanilide
   3,3',4-Trichlorocarbanilide Another class of antibacterial agents, which are useful in the present invention, are the so-called "natural" antibacterial actives, referred to as natural essential oils. These actives derive their names from their natural occurrence in plants.

Typical natural essential oil antibacterial actives include oils of anise, lemon, orange, rosemary, wintergreen, thyme, lavender, cloves, hops, tea tree, citronella, wheat, barley, lemongrass, cedar leaf, cedarwood, cinnamon, fleagrass, geranium, sandalwood, violet, cranberry, eucalyptus, vervain, peppermint, gum benzoin, basil, fennel, fir, balsam, menthol, ocmea origanum, *Hydastis carradensis, Berberidaceae daceae*, Ratanhiae and *Curcuma longa*. Also included in this class of natural essential oils are the key chemical components of the plant oils which have been found to provide the antimicrobial benefit. These chemicals include, but are not limited to anethol, catechole, camphene, carvacol, eugenol, eucalyptol, ferulic acid, farnesol, hinokitiol, tropolone, limonene, menthol, methyl salicylate, thymol, terpineol, verbenone, berberine, ratanhiae extract, caryophellene oxide, citronellic acid, curcumin, nerolidol and geraniol.

Additional active agents are antibacterial metal salts. This class generally includes salts of metals in groups 3b–7b, 8 and 3a–5a. Specifically are the salts of aluminum, zirconium, zinc, silver, gold, copper, lanthanum, tin, mercury, bismuth, selenium, strontium, scandium, yttrium, cerium, praseodymiun, neodymium, promethum, samarium, europium, gadolinium, terbium, dysprosium, holmium, erbium, thulium, ytterbium, lutetium and mixtures thereof.

Preferred antimicrobial agents for use herein are the broad spectrum actives selected from the group consisting of Triclosan®, Triclocarban®, Octopirox®, PCMX, ZPT, natural essential oils and their key ingredients, and mixtures thereof. The most preferred antimicrobial active for use in the present invention is Triclosan®.

B. Anionic Surfactant

The leave-on antimicrobial compositions of the present invention comprise from about 0.05% to about 10, preferably from about 0.1 to about 4%, and more preferably from about 0.2% to about 1%, by weight of the cleansing composition, of an anionic surfactant. Without being limited by theory, it is believed that the anionic surfactant disrupts the lipid in the cell membrane of the bacteria. The particular acid used herein reduces the negative charges on the cell wall of the bacteria, crosses through the cell membrane, weakened by the surfactant, and acidifies the cytoplasm of the bacteria. The antimicrobial active can then pass more easily through the weakened cell wall, and more efficiently poison the bacteria. Nonlimiting examples of anionic lathering surfactants useful in the compositions of the present invention are disclosed in McCutcheon's, *Detergents and Emulsifiers*, North American edition (1990), published by The Manufacturing Confectioner Publishing Co.; McCutcheon's, *Functional Materials*, North American Edition (1992); and U.S. Pat. No. 3,929,678, to Laughlin et al., issued Dec. 30, 1975, all of which are incorporated by reference.

A wide variety of anionic surfactants are potentially useful herein. Nonlimiting examples of anionic lathering surfactants include those selected from the group consisting of alkyl and alkyl ether sulfates, sulfated monoglycerides, sulfonated olefins, alkyl aryl sulfonates, primary or secondary alkane sulfonates, alkyl sulfosuccinates, acyl taurates, acyl isethionates, alkyl glycerylether sulfonate, sulfonated methyl esters, sulfonated fatty acids, alkyl phosphates, acyl glutamates, acyl sarcosinates, alkyl sulfoacetates, acylated peptides, alkyl ether carboxylates, acyl lactylates, anionic fluorosurfactants, and mixtures thereof. Mixtures of anionic surfactants can be used effectively in the present invention.

Anionic surfactants for use in the cleansing compositions include alkyl and alkyl ether sulfates. These materials have the respective formulae $R^1O-SO_3M$ and $R^1(CH_2H_4O)_x-O-SO_3M$, wherein $R^1$ is a saturated or unsaturated, branched or unbranched alkyl group from about 8 to about 24 carbon atoms, x is 1 to 10, and M is a water-soluble cation such as ammonium, sodium, potassium, magnesium, triethanolamine, diethanolamine and monoethanolamine. The alkyl sulfates are typically made by the sulfation of monohydric alcohols (having from about 8 to about 24 carbon atoms) using sulfur trioxide or other known sulfation technique. The alkyl ether sulfates are typically made as condensation products of ethylene oxide and monohydric alcohols (having from about 8 to about 24 carbon atoms) and then sulfated. These alcohols can be derived from fats, e.g., coconut oil or tallow, or can be synthetic. Specific examples of alkyl sulfates which may be used in the cleanser compositions are sodium, ammonium, potassium, magnesium, or TEA salts of lauryl or myristyl sulfate. Examples of alkyl ether sulfates which may be used include ammonium, sodium, magnesium, or TEA laureth-3 sulfate.

Another suitable class of anionic surfactants are the sulfated monoglycerides of the form $R^1CO-O-CH_2-C(OH)H-CH_2-O-SO_3M$, wherein $R^1$ is a saturated or unsaturated, branched or unbranched alkyl group from about 8 to about 24 carbon atoms, and M is a water-soluble cation such as ammonium, sodium, potassium, magnesium, triethanolamine, diethanolamine and monoethanolamine. These are typically made by the reaction of glycerin with fatty acids (having from about 8 to about 24 carbon atoms) to form a monoglyceride and the subsequent sulfation of this monoglyceride with sulfur trioxide. An example of a sulfated monoglyceride is sodium cocomonoglyceride sulfate.

Other suitable anionic surfactants include olefin sulfonates of the form $R^1SO_3M$, wherein $R^1$ is a mono-olefin having from about 12 to about 24 carbon atoms, and M is a water-soluble cation such as ammonium, sodium, potassium, magnesium, triethanolamine, diethanolamine and monoethanolamine. These compounds can be produced by the sulfonation of alpha olefins by means of uncomplexed sulfur trioxide, followed by neutralization of the acid reaction mixture in conditions such that any sultones which have been formed in the reaction are hydrolyzed to give the corresponding hydroxyalkanesulfonate. An example of a sulfonated olefin is sodium $C_{14}-C_{16}$ alpha olefin sulfonate. Other suitable anionic surfactants are the linear alkylbenzene sulfonates of the form $R^1-C_6H_4-SO_3M$, wherein $R^1$ is a saturated or unsaturated, branched or unbranched alkyl group from about 8 to about 24 carbon atoms, and M is a water-soluble cation such as ammonium, sodium, potassium, magnesium, triethanolamine, diethanolamine and monoethanolamine. These are formed by the sulfonation of linear alkyl benzene with sulfur trioxide. An example of this anionic surfactant is sodium dodecylbenzene sulfonate.

Still other anionic surfactants suitable for this cleansing composition include the primary or secondary alkane sulfonates of the form $R^1SO_3M$, wherein $R^1$ is a saturated or unsaturated, branched or unbranched alkyl chain from about 8 to about 24 carbon atoms, and M is a water-soluble cation such as ammonium, sodium, potassium, magnesium, triethanolamine, diethanolamine and monoethanolamine. These are commonly formed by the sulfonation of paraffins using sulfur dioxide in the presence of chlorine and ultraviolet light or another known sulfonation method. The sulfonation can occur in either the secondary or primary positions of the alkyl chain. An example of an alkane sulfonate useful herein is alkali metal or ammonium $C_{13}-C_{17}$ paraffin sulfonates.

Still other suitable anionic surfactants are the alkyl sulfosuccinates, which include disodium N-octadecylsulfosuccinamate; diammonium lauryl sulfosuccinate; tetrasodium N-(1,2-dicarboxyethyl)-N-octadecylsulfosuccinate; diamyl ester of sodium sulfosuccinic acid; dihexyl ester of sodium sulfosuccinic acid; and dioctyl esters of sodium sulfosuccinic acid.

Also useful are taurates which are based on taurine, which is also known as 2-aminoethanesulfonic acid. Examples of taurates include N-alkyltaurines such as the one prepared by reacting dodecylamine with sodium isethionate according to the teaching of U.S. Pat. No. 2,658,072 which is incorporated herein by reference in its entirety. Other examples based of taurine include the acyl taurines formed by the reaction of n-methyl taurine with fatty acids (having from about 8 to about 24 carbon atoms).

Another class of anionic surfactants suitable for use in the cleansing composition are the acyl isethionates. The acyl isethionates typically have the formula $R^1CO—O—CH_2CH_2SO_3M$ wherein $R^1$ is a saturated or unsaturated, branched or unbranched alkyl group having from about 10 to about 30 carbon atoms, and M is a cation. These are typically formed by the reaction of fatty acids (having from about 8 to about 30 carbon atoms) with an alkali metal isethionate. Nonlimiting examples of these acyl isethionates include ammonium cocoyl isethionate, sodium cocoyl isethionate, sodium lauroyl isethionate, and mixtures thereof.

Still other suitable anionic surfactants are the alkylglyceryl ether sulfonates of the form $R^1—OCH_2—C(OH)H—CH_2—SO_3M$, wherein $R^1$ is a saturated or unsaturated, branched or unbranched alkyl group from about 8 to about 24 carbon atoms, and M is a water-soluble cation such as ammonium, sodium, potassium, magnesium, triethanolamine, diethanolamine and monoethanolamine. These can be formed by the reaction of epichlorohydrin and sodium bisulfite with fatty alcohols (having from about 8 to about 24 carbon atoms) or other known methods. One example is sodium cocoglyceryl ether sulfonate. Other suitable anionic surfactants include the sulfonated fatty acids of the form $R^1—CH(SO_4)—COOH$ and sulfonated methyl esters of the from $R^1—CH(SO_4)—CO—O—CH_3$, where $R^1$ is a saturated or unsaturated, branched or unbranched alkyl group from about 8 to about 24 carbon atoms. These can be formed by the sulfonation of fatty acids or alkyl methyl esters (having from about 8 to about 24 carbon atoms) with sulfur trioxide or by another known sulfonation technique. Examples include alpha sulphonated coconut fatty acid and lauryl methyl ester.

Other anionic materials include phosphates such as monoalkyl, dialkyl, and trialkylphosphate salts formed by the reaction of phosphorous pentoxide with monohydric branched or unbranched alcohols having from about 8 to about 24 carbon atoms. These could also be formed by other known phosphation methods. An example from this class of surfactants is sodium mono or dilaurylphosphate.

Other anionic materials include acyl glutamates corresponding to the formula $R^1C—N(COOH)—CH_2CH_2—CO_2M$ wherein $R^1$ is a saturated or unsaturated, branched or unbranched alkyl or alkenyl group of about 8 to about 24 carbon atoms, and M is a water-soluble cation. Nonlimiting examples of which include sodium lauroyl glutamate and sodium cocoyl glutamate.

Other anionic materials include alkanoyl sarcosinates corresponding to the formula $R^1CON(CH_3)—CH_2CH_2—CO_2M$ wherein $R^1$ is a saturated or unsaturated, branched or unbranched alkyl or alkenyl group of about 10 to about 20 carbon atoms, and M is a water-soluble cation. Nonlimiting examples of which include sodium lauroyl sarcosinate, sodium cocoyl sarcosinate, and ammonium lauroyl sarcosinate.

Other anionic materials include alkyl ether carboxylates corresponding to the formula $R^1—(OCH_2CH_2)_x—OCH_2—CO_2M$ wherein $R^1$ is a saturated or unsaturated, branched or unbranched alkyl or alkenyl group of about 8 to about 24 carbon atoms, x is 1 to 10, and M is a water-soluble cation. Nonlimiting examples of which include sodium laureth carboxylate.

Other anionic materials include acyl lactylates corresponding to the formula $R^1CO—[O—CH(CH_3)—CO]_x—CO_2M$ wherein $R^1$ is a saturated or unsaturated, branched or unbranched alkyl or alkenyl group of about 8 to about 24 carbon atoms, x is 3, and M is a water-soluble cation. Nonlimiting examples of which include sodium cocoyl lactylate.

Other anionic materials include the carboxylates, nonlimiting examples of which include sodium lauroyl carboxylate, sodium cocoyl carboxylate, and ammonium lauroyl carboxylate. Anionic flourosurfactants can also be used.

Any counter cation, M, can be used on the anionic surfactant. Preferably the counter cation is selected from the group consisting of sodium, potassium, ammonium, monoethanolamine, diethanolamine, and triethanolamine. More preferably the counter cation is ammonium.

Nonlimiting examples of preferred anionic surfactants useful herein include those selected from the group consisting of sodium and ammonium alkyl sulfates and ether sulfates having chain lengths of predominantly 12 and 14 carbon atoms, olefin sulfonates having chain lengths of predominantly 14 and 16 carbon atoms, and paraffin sulfonates having chain lengths of from 13 to 17 carbon atoms, and mixtures thereof. More preferred for use herein is ammonium and sodium lauryl sulfate, ammonium and sodium myristyl sulfate, ammonium and sodium laureth-1, laureth-2, laureth-3, and laureth-4 sulfates, C14–C16 olefin sulfonates, C13–C17 paraffin sulfonates, and mixtures thereof. Most preferred is ammonium lauryl sulfate.

Another class of preferred anionic surfactants consist of surfactants which have a pKa of greater than about 4.0. These acidic surfactants include the group consisting of acyl sarcosinates, acyl glutamates, alkyl ether carboxylates and mixtures thereof. Acidic surfactants have been found to be a more efficacious surfactant. Without being limited by theory, it is believed that these surfactants provide both the acid and anionic surfactant benefit in one component. Leave-on antimicrobial compositions comprising these acidic surfactants provide better antimicrobial efficacy than other surfactants. Their acidic property also allows to the use of less separate proton dontaing agent, which even further improves the mildness of the leave-on antimicrobial compositions herein. When used, the acidic surfactants are used in the cleansing compositions herein at levels from about 0.1% to about 10%, preferably from about 0.2% to about 8%, more preferably from about 0.3% to about 5%, even more preferably from about 0.4% to about 2%, and most preferably from about 0.5% to about 1%.

Non-anionic surfactants of the group consisting of non-ionic surfactants, cationic surfactants, amphoteric surfactants and mixtures thereof, have been found to actually inhibit residual effectiveness benefits. It is believed that these surfactants interfere with the anionic surfactant disruption of the lipid in the cell membrane. The ratio of the amount of these non-anionic surfactants to the amount of anionic surfactant should be less than 1:1, preferably less than 1:2, and more preferably less than 1:4 in the compositions herein.

The leave-on antimicrobial compositions of the present invention preferably do not comprise hydrotropic sulfonates, particularly salts of terpenoids, or mono- or binuclear aromatic compounds such as sulfonates of camphor, toluene, xylene, cumene and naphthene.

Proton Donating Agent

The leave-on antimicrobial compositions of the present invention comprise from about 0.1% to about 10%, preferably from about 0.5% to about 8%, more preferably from about 1% to about 5%, based on the weight of the personal cleansing composition, of a proton donating agent. By "proton donating agent" it is meant any acid compound or mixture thereof, which results in undissociated acid on the skin after use. Proton donating agents can be organic acids, including polymeric acids, mineral acids or mixtures thereof.

Organic Acids

Proton donating agents which are organic acids which remain at least partially undissociated in the neat composition. These organic proton donating agents can be added directly to the composition in the acid form or can be formed by adding the conjugate base of the desired acid and a sufficient amount of a separate acid strong enough to form the undissociated acid from the base.

Buffering Capacity

Preferred organic proton donating agents are selected and formulated based on their buffer capacity and pKa. Buffer capacity is defined as the amount of protons (weight %) available in the formulation at the product pH for those acid groups with pKa's less than about 6.0. Buffer capacity can be either calculated using pKa's, pH, and the concentrations of the acids and conjugate bases, ignoring any pKa greater than 6.0, or it can be determined experimentally through a simple acid-base titration using sodium hydroxide or potassium hydroxide using an endpoint of pH equals 6.0.

Preferred organic proton donating agents of the antibacterial cleansing composition herein have a buffer capacity of greater than about 0.005%, more preferably greater than about 0.01%, even more preferably greater than about 0.02%, and most preferably greater than about 0.04%.

Mineral Acids

Proton donating agents which are mineral acids will not remain undissociated in the neat composition. Despite this, it has been found that mineral acids can be effective proton donating agents for use herein. Without being limited by theory, it is believed that the strong mineral acid, acidify the carboxylic and phosphatidyl groups in proteins of the skin cells, thereby providing in-situ undissociated acid. These proton donating agents can only be added directly to the composition in the acid form.

pH

It is critical to achieving the benefits of the invention that the undissociated acid from the proton donating agent (deposited or formed in-situ) remain on the skin in the protonated form. Therefore, the pH of the leave-on antimicrobial compositions of the present invention must be adjusted to a sufficiently low level in order to either form or deposit substantial undissociated acid on the skin. The pH of the compositions should be adjusted and preferably buffered to range from about 3.0 to about 6.0, preferably from about 3.5 to about 5.0 and more preferably from about 3.5 to about 4.5.

A non-exclusive list of examples of organic acids which can be used as the proton donating agent are adipic acid, tartaric acid, citric acid, maleic acid, malic acid, succinic acid, glycolic acid, glutaric acid, benzoic acid, malonic acid, salicylic acid, gluconic acid, polyacrylic acid, their salts, and mixtures thereof. Especially preferred organic proton donating agents are the group consisting of malic acid, malonic acid, citric acid, succinic acid and lactic acid. A non-exclusive list of examples of mineral acid for use herein are hydrochloric, phosphoric, sulfuric and mixtures thereof.

Salicylic acid has been found to be a more preferred proton donating agent. Leave-on antimicrobial compositions comprising salicylic acid provide better antimicrobial efficacy than other proton donating agents. When used, salicylic acid is used in the leave-on compositions herein at a level of from about 0.15% to about 2.0%.

Water

The leave-on antimicrobial compositions of the present invention comprise from about 0% to about 99.85%, preferably from about 3% to about 98%, more preferably from about 5% to about 97.5%, and most preferably from about 38% to about 95.99% water.

Preferable Optional Ingredients

Mildness Enhancers

In order to achieve the mildness required of the present invention, optional ingredients to enhance the mildness to the skin can be added. These ingredients include cationic and nonionic polymers, co-surfactants, moisturizers and mixtures thereof. Polymers useful herein include polyethylene glycols, polypropylene glycols, hydrolyzed silk proteins, hydrolyzed milk proteins, hydrolyzed keratin proteins, guar hydroxypropyltrimonium chloride, polyquats, silicone polymers and mixtures thereof. When used, the mildness enhancing polymers comprise from about 0.1% to about 1%, preferably from about 0.2% to about 1.0%, and more preferably from about 0.2% to about 0.6%, by weight of the leave-on antimicrobial composition, of the composition. Co-surfactants useful herein include nonionic surfactants such as the Genapol® 24 series of ethoxylated alcohols, POE(20) sorbitan monooleate (Tween® 80), polyethylene glycol cocoate and Pluronic® propylene oxide/ethylene oxide block polymers, and amphoteric surfactants such as alkyl betaines, alkyl sultaines, alkyl amphoacetates, alkyl amphodiacetates, alkyl amphopropionates, and alkyl amphodipropionates. When used, the mildness enhancing cosurfactants comprise from about 20% to about 70%, preferably from about 20% to about 50%, by weight of the anionic surfactant, of the leave-on composition.

Another group of mildness enhancers are lipid skin moisturizing agents which provide a moisturizing benefit to the user of the leave-on antimicrobial composition when the lipophilic skin moisturizing agent is deposited to the user's skin. When used in the antimicrobial compositions herein, lipophilic skin moisturizing agents are used, they are employed at a level of about 0.1% to about 30%, preferably from about 0.2% to about 10%, most preferably from about 0.5% to about 5% by weight of the composition.

In some cases, the lipophilic skin moisturizing agent can desirably be defined in terms of its solubility parameter, as defined by *Vaughan in Cosmetics and Toiletries,* Vol. 103, p. 47–69, October 1988. A lipophilic skin moisturizing agent having a Vaughan solubility Parameter (VSP) from 5 to 10, preferably from 5.5 to 9 is suitable for use in the antimicrobial compositions herein.

A wide variety of lipid type materials and mixtures of materials are suitable for use in the leave-on antimicrobial compositions of the present invention. Preferably, the lipophilic skin conditioning agent is selected from the group consisting of hydrocarbon oils and waxes, silicones, fatty acid derivatives, cholesterol, cholesterol derivatives, di- and tri-glycerides, vegetable oils, vegetable oil derivatives, liquid nondigestible oils such as those described in U.S. Pat. Nos. 3,600,186 to Mattson; Issued Aug. 17, 1971 and 4,005,195 and 4,005,196 to Jandacek et al; both issued Jan.

25, 1977, all of which are herein incorporated by reference, or blends of liquid digestible or nondigestible oils with solid polyol polyesters such as those described in U.S. Pat. No. 4,797,300 to Jandacek; issued Jan. 10, 1989; U.S. Pat. Nos. 5,306,514, 5,306,516 and 5,306,515 to Letton; all issued Apr. 26, 1994, all of which are herein incorporated by reference, and acetoglyceride esters, alkyl esters, alkenyl esters, lanolin and its derivatives, milk tri-glycerides, wax esters, beeswax derivatives, sterols, phospholipids and mixtures thereof. Fatty acids, fatty acid soaps and water soluble polyols are specifically excluded from our definition of a lipophilic skin moisturizing agent.

Hydrocarbon oils and waxes: Some examples are petrolatum, mineral oil microcrystalline waxes, polyalkenes (e.g. hydrogenated and nonhydrogenated polybutene and polydecene), paraffins, cerasin, ozokerite, polyethylene and perhydrosqualene. Blends of petrolatum and hydrogenated and nonhydrogenated high molecular weight polybutenes wherein the ratio of petrolatum to polybutene ranges from about 90:10 to about 40:60 are also suitable for use as the lipid skin moisturizing agent in the compositions herein.

Silicone Oils: Some examples are dimethicone copolyol, dimethylpolysiloxane, diethylpolysiloxane, high molecular weight dimethicone, mixed C1–C30 alkyl polysiloxane, phenyl dimethicone, dimethiconol, and mixtures thereof. More preferred are non-volatile silicones selected from dimethicone, dimethiconol, mixed C1–C30 alkyl polysiloxane, and mixtures thereof. Nonlimiting examples of silicones useful herein are described in U.S. Pat. No. 5,011,681, to Ciotti et al., issued Apr. 30, 1991, which is incorporated by reference.

Di- and tri-glycerides: Some examples are castor oil, soy bean oil, derivatized soybean oils such as maleated soy bean oil, safflower oil, cotton seed oil, corn oil, walnut oil, peanut oil, olive oil, cod liver oil, almond oil, avocado oil, palm oil and sesame oil, vegetable oils and vegetable oil derivatives; coconut oil and derivatized coconut oil, cottonseed oil and derivatized cottonseed oil, jojoba oil, cocoa butter, and the like.

Acetoglyceride esters are used and an example is acetylated monoglycerides.

Lanolin and its derivatives are preferred and some examples are lanolin, lanolin oil, lanolin wax, lanolin alcohols, lanolin fatty acids, isopropyl lanolate, acetylated lanolin, acetylated lanolin alcohols, lanolin alcohol linoleate, lanolin alcohol riconoleate.

It is most preferred when at least 75% of the lipophilic skin conditioning agent is comprised of lipids selected from the group consisting: petrolatum, blends of petrolatum and high molecular weight polybutene, mineral oil, liquid nondigestible oils (e.g. liquid cottonseed sucrose octaesters) or blends of liquid digestible or nondigestible oils with solid polyol polyesters (e.g. sucrose octaesters prepared from C22 fatty acids) wherein the ratio of liquid digestible or nondigestible oil to solid polyol polyester ranges from about 96:4 to about 80:20, hydrogenated or nonhydrogenated polybutene, microcrystalline wax, polyalkene, paraffin, cerasin, ozokerite, polyethylene, perhydrosqualene; dimethicones, alkyl siloxane, polymethylsiloxane, methylphenylpolysiloxane and mixtures thereof. When as blend of petrolatum and other lipids is used, the ratio of petrolatum to the other selected lipids (hydrogenated or unhydrogenated polybutene or polydecene or mineral oil) is preferably from about 10:1 to about 1:2, more preferably from about 5:1 to about 1:1.

Stabilizers

When a lipophilic skin moisturizing agent is employed as the mildness enhancer in the antimicrobial compositions herein, a stabilizer may also be included at a level ranging from about 0.1% to about 10%, preferably from about 0.1% to about 8%, more preferably from about 0.1% to about 5% by weight of the leave-on antimicrobial composition.

The stabilizer is used to form a crystalline stabilizing network in the liquid composition that prevents the lipophilic skin moisturizer agent droplets from coalescing and phase splitting in the product. The network exhibits time dependent recovery of viscosity after shearing (e.g., thixotropy).

The stabilizers used herein are not surfactants. The stabilizers provide improved shelf and stress stability. Some preferred hydroxyl-containing stabilizers include 12-hydroxystearic acid, 9,10-dihydroxystearic acid, tri-9, 10-dihydroxystearin and tri-12-hydroxystearin (hydrogenated castor oil is mostly tri-12-hydroxystearin). Tri-12-hydroxystearin is most preferred for use in the compositions herein. When these crystalline, hydroxyl-containing stabilizers are utilized in the leave-on compositions herein, they are typically present at from about 0.1% to 10%, preferably from 0.1% to 8%, more preferably from 0.1% to about 5% of the antimicrobial compositions. The stabilizer is insoluble in water under ambient to near ambient conditions.

Alternatively, the stabilizer employed in the leave-on compositions herein can comprise a polymeric thickener. When polymeric thickeners as the stabilizer in the leave-on compositions herein, they are typically included in an amount ranging from about 0.01% to about 5%, preferably from about 0.3% to about 3%, by weight of the composition. The polymeric thickener is preferably an anionic, nonionic, cationic or hydrophobically modifier polymer selected from the group consisting of cationic polysaccharides of the cationic guar gum class with molecular weights of 1,000 to 3,000,000, anionic, cationic, and nonionic homopolymers derived from acrylic and/or methacrylic acid, anionic, cationic, and nonionic cellulose resins, cationic copolymers of dimethyldialkylammonium chloride, and acrylic acid, cationic homopolymers of dimethylalkylammonium chloride, cationic polyalklene, and ethoxypolyalkylene imines, polyethylene glycol of molecular weight from 100,000 to 4,000,000, and mixtures thereof. Preferably, the polymer is selected from the group consisting of sodium polyacrylate, hydroxy ethyl cellulose, cetyl hydroxy ethyl cellulose, and Polyquaternium 10.

Alternatively, the stabilizer employed in the leave-on compositions herein can comprise C10–C22 ethylene glycol fatty acid esters. C10–C22 ethylene glycol fatty acid esters can also desirably be employed in combination with the polymeric thickeners hereinbefore described. The ester is preferably a diester, more preferably a C14–C18 diester, most preferably ethylene glycol distearate. When C10–C22 ethylene glycol fatty acid esters are utilized as the stabilizer in the leave-on antimicrobial compositions herein, they are typically present at from about 3% to about 10%, preferably from about 5% to about 8%, more preferably from about 6% to about 8% of the leave-on antimicrobial composition. Another class of stabilizer which can be employed in the antimicrobial compositions of the present invention comprises dispersed amorphous silica selected from the group consisting of fumed silica and precipitated silica and mixtures thereof. As used herein the term "dispersed amorphous silica" refers to small, finely divided non-crystalline silica having a mean agglomerate particle size of less than about 100 microns.

Fumed silica, which is also known as arced silica, is produced by the vapor phase hydrolysis of silicon tetrachloride in a hydrogen oxygen flame. It is believed that the combustion process creates silicone dioxide molecules which condense to form particles. The particles collide, attach and sinter together. The result of this process is a three dimensional branched chain aggregate. Once the aggregate cools below the fusion point of silica, which is about 1710° C., further collisions result in mechanical entanglement of the chains to form agglomerates. Precipitated silicas and silica gels are generally made in aqueous solution. See, Cabot Technical Data Pamphlet TD-100 entitled "CAB-O-SIL® Untreated Fumed Silica Properties and Functions", October 1993, and Cabot Technical Dat Pamphlet TD-104 entitled "CAB-O-SIL® Fumed Silica in Cosmetic and Personal Care Products", March 1992, both of which are herein incorporated by reference.

The fumed silica preferably has a mean agglomerate particle size ranging from about 0.1 microns to about 100 microns, preferably from about I micron to about 50 microns, and more preferably from about 10 microns to about 30 microns. The agglomerates are composed of aggregates which have a mean particle size ranging from about 0.01 microns to about 15 microns, preferably from about 0.05 microns to about 10 microns, more preferably from about 0.1 microns to about 5 microns and most preferably from about 0.2 microns to about 0.3 microns. The silica preferably has a surface area greater than 50 sq. m/gram, more preferably greater than about 130 sq. m./gram, most preferably greater than about 180 sq. m./gram.

When amorphous silicas are used as the stabilizer herein, they are typically included in the leave-on compositions at levels ranging from about 0.1% to about 10%, preferably from about 0.25% to about 8%, more preferably from about 0.5% to about 5%.

A fourth class of stabilizer which can be employed in the leave-on antimicrobial compositions of the present invention comprises dispersed smectite clay selected from the group consisting of bentonite and hectorite and mixtures thereof. Bentonite is a colloidal aluminum clay sulfate. See Merck Index, Eleventh Edition, 1989, entry 1062, p. 164, which is incorporated by reference. Hectorite is a clay containing sodium, magnesium, lithium, silicon, oxygen, hydrogen and flourine. See Merck Index, eleventh Edition, 1989, entry 4538, p. 729, which is herein incorporated by reference.

When smectite clay is employed as the stabilizer in the leave-on compositions of the present invention, it is typically included in amounts ranging from about 0.1% to about 10%, preferably from about 0.25% to about 8%, more preferably from about 0.5% to about 5%. Other known stabilizers, such as fatty acids and fatty alcohols, can also be employed in the compositions herein. Palmitic acid and lauric acid are especially preferred for use herein.

Other Optional Ingredients

The compositions of the present invention can comprise a wide range of optional ingredients. The *CTFA International Cosmetic Ingredient Dictionary,* Sixth Edition, 1995, which is incorporated by reference herein in its entirety, describes a wide variety of nonlimiting cosmetic and pharmaceutical ingredients commonly used in the skin care industry, which are suitable for use in the compositions of the present invention. Nonlimiting examples of functional classes of ingredients are described at page 537 of this reference. Examples of these functional classes include: abrasives, anti-acne agents, anticaking agents, antioxidants, binders, biological additives, bulking agents, chelating agents, chemical additives, colorants, cosmetic astringents, cosmetic biocides, denaturants, drug astringents, emulsifiers, external analgesics, film formers, fragrance components, humectants, opacifying agents, plasticizers, preservatives, propellants, reducing agents, skin bleaching agents, skin-conditioning agents (emollient, humectants, miscellaneous, and occlusive), skin protectants, solvents, foam boosters, hydrotropes, solubilizing agents, suspending agents (nonsurfactant), sunscreen agents, ultraviolet light absorbers, and viscosity increasing agents (aqueous and nonaqueous). Examples of other functional classes of materials useful herein that are well known to one of ordinary skill in the art include solubilizing agents, sequestrants, and keratolytics, and the like.

II. Methods of Manufacture of the Leave-on Antimicrobial Compositions

The leave-on antimicrobial compositions of the present invention are made via art recognized techniques for the various forms of leave-on products.

III. Methods of Using the Leave-on Antimicrobial Composition

The leave-on antimicrobial compositions of the present invention are useful for reducing the number of germs on the skin and controlling the spread of Gram negative and Gram positive bacteria over time. Typically, a suitable or effective amount of the composition is applied to the area to be treated. Alternatively, a suitable amount of the topical composition can be applied via intermediate application to a washcloth, sponge, pad, cotton ball, puff or other application device. Generally, an effective amount of product to be used will depend upon the needs and usage habits of the individual. Typical amounts of the present compositions useful for cleansing range from about 0.1 mg/cm$^2$ to about 10 mg/cm$^2$, preferably from about 0.6 mg/cm$^2$ to about 5 mg/cm$^2$ skin area to be cleansed.

EXAMPLES

The following examples further describe and demonstrate embodiments within the scope of the present invention. In the following examples, all ingredients are listed at an active level. The examples are given solely for the purpose of illustration and are not to be construed as limitations of the present invention, as many variations thereof are possible without departing from the spirit and scope of the invention.

Ingredients are identified by chemical or CTFA name.

Fifteen leave-on antimicrobial compositions are prepared according to the tables below.

| Leave-on Antimicrobial Compositions | | | | | |
|---|---|---|---|---|---|
| Component | Ex. 1 | Ex. 2 | Ex. 3 | Ex. 4 | Ex. 5 |
| Mineral oil | 1.00% | 1.00% | 1.00% | 1.00% | 0.00% |
| Propylene glycol | 1.00% | 1.00% | 1.00% | 1.00% | 1.00% |
| Ammonium Lauryl Sulfate | 0.60% | 0.60% | 0.60% | 0.60% | 0.60% |
| Citric Acid | 4.00% | 0.00% | 0.00% | 0.00% | 0.00% |
| Sodium Citrate | 3.30% | 0.00% | 2.00% | 0.00% | 0.00% |
| Succinic Acid | 0.00% | 4.00% | 0.00% | 0.00% | 4.00% |
| Sodium Succinate | 0.00% | 3.30% | 0.00% | 0.00% | 3.20% |
| Malic Acid | 0.00% | 0.00% | 2.50% | 0.00% | 0.00% |
| Malonic Acid | 0.00% | 0.00% | 0.00% | 4.00% | 0.00% |
| Sodium Malonate | 0.00% | 0.00% | 0.00 | 3.20% | 0.00% |
| Steareth 20 | 0.55% | 0.55% | 0.55% | 0.55% | 0.00% |
| Steareth 2 | 0.45% | 0.45% | 0.45% | 0.45% | 0.00% |
| Triclosan ® | 0.15% | 0.15% | 0.15% | 0.15% | 0.15% |
| Miscellaneous | 0.36% | 0.36% | 0.36% | 0.36% | 0.36% |

-continued

Leave-on Antimicrobial Compositions

| Water | q.s. | q.s. | q.s. | q.s. | q.s. |
|---|---|---|---|---|---|
| pH | 4.0 | 4.5 | 3.9 | 3.9 | 3.9 |

| Component | Ex. 6 | Ex. 7 | Ex. 8 | Ex. 9 | Ex. 10 |
|---|---|---|---|---|---|
| Mineral oil | 0.00% | 0.00% | 1.00% | 1.00% | 1.00% |
| Propylene glycol | 1.00% | 1.00% | 1.00% | 1.00% | 1.00% |
| Ammonium Lauryl Sulfate | 0.60% | 0.60% | 0.60% | 0.60% | 1.00% |
| Citric Acid | 0.00% | 0.00% | 2.50% | 2.50% | 4.00% |
| Sodium Citrate | 0.00% | 3.70% | 2.00% | 2.00% | 3.20% |
| Succinic Acid | 4.60% | 0.00% | 0.00% | 0.00% | 0.00% |
| Sodium Succinate | 3.00% | 0.00% | 0.00% | 0.00% | 0.00% |
| Malic Acid | 0.00% | 4.00% | 0.00% | 0.00% | 0.00% |
| Steareth 20 | 0.55% | 0.00 | 0.55% | 0.08% | 0.28% |
| Steareth 2 | 0.45% | 0.00% | 0.45% | 0.07% | 0.23% |
| Oleth 20 | 0.00% | 0.00% | 0.00% | 0.80 | 0.28% |
| Oleth 2 | 0.00% | 0.00% | 0.00% | 0.07% | 0.23% |
| Triclosan ® | 0.00% | 0.50% | 0.50% | 0.15% | 0.25% |
| Thymol | 1.00% | 0.00% | 0.00% | 0.00% | 0.00% |
| Miscellaneous | 0.36% | 0.36% | 0.36% | 0.36% | 0.36% |
| Water | q.s. | q.s. | q.s. | q.s. | q.s. |
| pH | 3.2 | 5.0 | 3.9 | 3.9 | 3.9 |

| Component | Ex. 11 | Ex. 12 | Ex. 13 | Ex. 14 | Ex. 15 |
|---|---|---|---|---|---|
| Mineral oil | 1.00% | 1.00% | 1.00% | 1.00% | 1.00% |
| Propylene glycol | 1.00% | 1.00% | 1.00% | 1.00% | 1.00% |
| Ammonium Lauryl Sulfate | 0.00% | 0.00% | 0.00% | 0.00% | 0.60% |
| Ammonium Laureth Sulfate | 0.00% | 5.00% | 0.00% | 0.00% | 0.00% |
| Hostapur SAS 60 (SPS) | 1.00% | 0.00% | 0.00% | 0.00% | 0.00% |
| $C_{13}$–$C_{16}$ Sodium Alpha Olefin Sulfonate | 0.00% | 0.00% | 2.00% | 0.00% | 0.00% |
| Sodium Ladroyl Sarcosinate | 0.00% | 0.00% | 0.00% | 1.00% | 0.00% |
| Citric Acid | 0.055% | 7.50% | 0.00% | 0.00% | 0.00% |
| Sodium Citrate | 0.00% | 4.00% | 2.00% | 0.00% | 0.00% |
| Succinic Acid | 4.00% | 0.00% | 0.00% | 0.00% | 0.00% |
| Sodium Succinate | 0.67% | 0.00% | 0.00% | 0.00% | 0.00% |
| Malic Acid | 0.00% | 0.00% | 2.50% | 0.00% | 0.00% |
| Malonic Acid | 0.00% | 0.00% | 0.00% | 4.00% | 0.00% |
| Sodium Malonate | 0.00 | 0.00% | 0.00% | 3.20% | 0.00% |
| Salicylic Acid | 0.00% | 0.00% | 0.00% | 0.00% | 0.50% |
| Steareth 20 | 0.55% | 0.55% | 0.55% | 0.55% | 0.55% |
| Steareth 2 | 0.45% | 0.45% | 0.45% | 0.45% | 0.45% |
| Triclosan ® | 0.15% | 3.00% | 0.15% | 0.01% | 0.15% |
| Cocamidopropyl Betaine | 0.00% | 0.00% | 0.00% | 4.00% | 0.00% |
| Polyquat 10 | 0.00% | 0.00% | 0.00% | 0.40% | 0.00% |
| Miscellaneous | 0.36% | 0.36% | 0.36 | 0.36% | 0.36% |
| Water | q.s. | q.s. | q.s. | q.s. | q.s. |
| pH | 3–6 | 3–6 | 3–6 | 3–6 | 3–6 |

Procedure for Making Leave-on Antimicrobial Composition Examples

When mineral oil is used, premix mineral oil, propylene glycol, active, steareth 2 and 20, oleth 2 and 20, and 50%, by weight of the oil, glycol, active, steareth and oleth materials, water to a premix vessel. Heat to 165° F.±10° F. Add additional 50%, by weight of the oil, glycol, active, steareth and oleth materials, of water to the premix tank.

Add all but 5 weight percent of remaining water to second mix tank. If required, add premix to the mix tank. Add surfactants to mix tank. Heat materials to 155° F.±10° F. and mix until dissolved. Cool to less than 100° F., add acid and antibacterial active, if not in premix, and perfumes. Mix until materials are dissolved. Adjust pH to target with required buffer (NaOH or buffer salt). Add remaining water to complete product.

What is claimed is:

1. A leave-on antimicrobial composition comprising:
   a. from about 0.001% to about 5.0%, by weight of the leave-on antimicrobial composition, of an antimicrobial active;
   b. from about 0.05% to about 1%, by weight of the leave-on antimicrobial composition, of an anionic surfactant;
   c. from about 1% to about 10%, by weight of the leave-on antimicrobial composition, of a proton donating agent; and
   d. from about 0% to about 99.85%, by weight of the leave-on antimicrobial composition, water;
   wherein the composition is adjusted to a pH of from about 3.0 to about 6.0.

2. A leave-on antimicrobial composition according to claim 1 wherein the antimicrobial active is selected from the group consisting of triclosan, triclocarban, piroctone oleamine, PCMX, ZPT, natural essential oils and their key chemical components, and mixtures thereof.

3. A leave-on antimicrobial composition according to claim 2 wherein the proton donating agent is an organic acid having a Buffering Capacity of greater than about 0.005.

4. A leave-on antimicrobial composition according to claim 3 wherein the proton donating agent is selected from the group comprising adipic acid, tartaric acid, citric acid, maleic acid, malic acid, succinic acid, glycolic acid, glutaric acid, benzoic acid, malonic acid, salicylic acid, gluconic acid, polyacrylic acid, their salts, and mixtures thereof.

5. A leave-on antimicrobial composition according to claim 4 wherein the ratio of the amount of non-anionic surfactants to the amount of anionic surfactant in the antibacterial cleansing composition is less than 1:1.

6. A leave-on antimicrobial composition according to claim 5 wherein the composition is adjusted to a pH of from about 3.5 to about 5.0.

7. A leave-on antimicrobial composition according to claim 6, wherein the composition is adjusted to a pH of from about 3.5 to about 4.5.

8. A leave-on antimicrobial composition according to claim 7 wherein the antimicrobial active is triclosan.

9. A leave-on antimicrobial composition according to claim 8 wherein the proton donating agent is selected from the group consisting of malic acid, malonic acid, citric acid, succinic acid and lactic acid.

10. A leave-on antimicrobial composition according to claim 1 further comprising a mildness enhancing agent.

11. A leave-on antimicrobial composition according to claim 10 wherein the mildness enhancing agent is selected from the group consisting of from about 0.1% to about 1.0%, by weight of the antimicrobial composition, of a mildness enhancing polymer, from about 20% to about 70%, by weight of the anionic surfactant, of a mildness enhancing cosurfactant, and mixtures thereof.

12. A leave-on antimicrobial composition according to claim 10 wherein the mildness enhancing agent comprises a lipophilic skin moisturizing agent and the composition comprises from about 0.1% to about 30% of the lipophilic skin moisturizing agent.

13. A leave-on antimicrobial composition according to claim 1 further comprising from about 0.1% to about 10%, by weight of the cleansing composition, of an acidic surfactant.

14. A leave-on antimicrobial composition according to claim 1 wherein from about 0.15% to about 2%, by weight of the leave-on antimicrobial composition, of the proton donating agent is salicylic acid.

15. A method for providing residual effectiveness against transient Gram negative bacteria, improved residual effectiveness against Gram positive bacteria and improved immediate reduction of germs on the skin comprising the use of a safe and effective amount of the composition of claim 1 on human skin.

16. A method for providing residual effectiveness against transient Gram negative bacteria, improved residual effectiveness against Gram positive bacteria and improved immediate reduction of germs on the skin comprising the use of a safe and effective amount of the composition of claim 9 on human skin.

17. A method for providing residual effectiveness against transient Gram negative bacteria, improved residual effectiveness against Gram positive bacteria and improved immediate reduction of germs on the skin comprising the use of a safe and effective amount of the composition of claim 10 on human skin.

18. A method for providing residual effectiveness against transient Gram negative bacteria, improved residual effectiveness against Gram positive bacteria and improved immediate reduction of germs on the skin comprising the use of a safe and effective amount of the composition of claim 12 on human skin.

19. A method for providing residual effectiveness against transient Gram negative bacteria, improved residual effectiveness against Gram positive bacteria and improved immediate reduction of germs on the skin comprising the use of a safe and effective amount of the composition of claim 13 on human skin.

20. A method for providing residual effectiveness against transient Gram negative bacteria, improved residual effectiveness against Gram positive bacteria and improved immediate reduction of germs on the skin comprising the use of a safe and effective amount of the composition of claim 14 on human skin.

21. A method for treating acne comprising the use of a safe and effective amount of the composition of claim 1 on human skin.

22. A leave-on antimicrobial composition comprising:
 a. from about 0.001% to about 5.0%, by weight of the leave-on antimicrobial composition, of an antimicrobial active;
 b. from about 0.05% to about 4%, by weight of the leave-on antimicrobial composition, of an anionic surfactant selected from the group consisting of sodium and ammonium alkyl sulfates and ether sulfates having chain lengths of predominantly 12 and 14 carbon atoms, olefin sulfonates having chain lengths of predominantly 14 and 16 carbon atoms, and paraffin sulfonates having an average chain length of from 13 to 17 carbon atoms, and mixtures thereof;
 c. from about 0.1% to about 10%, by weight of the leave-on antimicrobial composition, of a proton donating agent; and
 d. from about 0% to about 99.85%, by weight of the leave-on antimicrobial composition, water;
wherein the composition is adjusted to a pH of from about 3.0 to about 6.0; and
wherein the ratio of the amount of non-anionic surfactants to the amount of anionic surfactant in the antibacterial composition is less than 1:1.

23. A leave-on antimicrobial composition according to claim 22 wherein the antimicrobial active is selected from the group consisting of triclosan, triclocarban, piroctone oleamine, PCMX, ZPT, natural essential oils and their key chemical components, and mixtures thereof.

24. A leave-on antimicrobial composition according to claim 23 wherein the proton donating agent is an organic acid having a Buffering Capacity of greater than about 0.005.

25. A leave-on antimicrobial composition according to claim 24 wherein the proton donating agent is selected from the group comprising adipic acid, tartaric acid, citric acid, maleic acid, malic acid, succinic acid, glycolic acid, glutaric acid, benzoic acid, malonic acid, salicylic acid, gluconic acid, polyacrylic acid, their salts, and mixtures thereof.

26. A leave-on antimicrobial composition according to claim 25 wherein the antimicrobial active is present at a level ranging from about 0.05% to about 2%, the anionic surfactant is present at a level of from about 0.1% to about 4%, and the proton donating agent is present at a level of from about 0.5% to about 8%.

27. A leave-on antimicrobial composition according to claim 26 wherein the composition is adjusted to a pH of from about 3.5 to about 5.0.

28. A leave-on antimicrobial composition according to claim 29 wherein the composition is adjusted to a pH of from about 3.5 to about 4.5.

29. A leave-on antimicrobial composition according to claim 28 wherein the antimicrobial active is triclosan.

30. A leave-on antimicrobial composition according to claim 29 wherein the proton donating agent is selected from the group consisting of malic acid, malonic acid, citric acid, succinic acid and lactic acid.

31. A leave-on antimicrobial composition according to claim 30 wherein the anionic surfactant is ammonium lauryl sulfate.

32. A leave-on antimicrobial composition according to claim 22 further comprising a mildness enhancing agent.

33. A leave-on antimicrobial composition according to claim 32 wherein the mildness enhancing agent is selected from the group consisting of from about 0.1% to about 1.0%, by weight of the antimicrobial composition, of a mildness enhancing polymer, from about 20% to about 70%, by weight of the anionic surfactant, of a mildness enhancing cosurfactant, and mixtures thereof.

34. A leave-on antimicrobial composition according to claim 22 wherein the mildness enhancing agent comprises a lipophilic skin moisturizing agent and the composition comprises from about 0.1% to about 30% of the lipophilic skin moisturizing agent.

35. A leave-on antimicrobial composition according to claim 22 further comprising from about 0.1% to about 10%, by weight of the cleansing composition, of an acidic surfactant.

36. A leave-on antimicrobial composition according to claim 22 wherein from about 0.15% to about 2%, by weight of the leave-on antimicrobial composition, of the proton donating agent is salicylic acid.

37. A method for providing residual effectiveness against transient Gram negative bacteria, improved residual effectiveness against Gram positive bacteria and improved immediate reduction of germs on the skin comprising the use of a safe and effective amount of the composition of claim 22 on human skin.

38. A method for providing residual effectiveness against transient Gram negative bacteria, improved residual effectiveness against Gram positive bacteria and improved immediate reduction of germs on the skin comprising the use of a safe and effective amount of the composition of claim 31 on human skin.

39. A method for providing residual effectiveness against transient Gram negative bacteria, improved residual effectiveness against Gram positive bacteria and improved immediate reduction of germs on the skin comprising the use of a safe and effective amount of the composition of claim 33 on human skin.

40. A method for providing residual effectiveness against transient Gram negative bacteria, improved residual effectiveness against Gram positive bacteria and improved immediate reduction of germs on the skin comprising the use of a safe and effective amount of the composition of claim 34 on human skin.

41. A method for providing residual effectiveness against transient Gram negative bacteria, improved residual effectiveness against Gram positive bacteria and improved immediate reduction of germs on the skin comprising the use of a safe and effective amount of the composition of claim 35 on human skin.

42. A method for providing residual effectiveness against transient Gram negative bacteria, improved residual effectiveness against Gram positive bacteria and improved immediate reduction of germs on the skin comprising the use of a safe and effective amount of the composition of claim 36 on human skin.

* * * * *